United States Patent [19]

Farooq

[11] 4,265,655

[45] May 5, 1981

[54] 2-OXO- AND 2-THIOXO-1,3-DITHIOL COMPOUNDS AS ACTIVE SUBSTANCES FOR REGULATING PLANT METABOLISM AND THEIR USE

[75] Inventor: Saleem Farooq, Ettingen, Switzerland

[73] Assignee: Ciba-Geigy Corporation, Ardsley, N.Y.

[21] Appl. No.: 44,297

[22] Filed: May 31, 1979

[30] Foreign Application Priority Data

Jun. 7, 1978 [CH] Switzerland .................. 6224/78

[51] Int. Cl.$^3$ ............... A01N 43/02; A01N 43/00
[52] U.S. Cl. ........................... 71/90; 71/88; 260/340.6; 260/340.9 R; 549/37
[58] Field of Search ............... 71/90, 88; 260/327 A

[56] References Cited

U.S. PATENT DOCUMENTS

| | | | |
|---|---|---|---|
| 3,187,009 | 6/1965 | Klingsberg | 260/327 |
| 3,211,749 | 10/1965 | Klingsberg | 260/327 |
| 3,758,503 | 9/1973 | Hartzler | 260/327 M |

OTHER PUBLICATIONS

Marita, M., and C. U. Pittmann. "Synthesis", 1976, pp. 496-514

Melby et al., J. Org. Chem. 39,245 (1974).

*Primary Examiner*—Glennon H. Hollrah
*Attorney, Agent, or Firm*—Frederick H. Rabin

[57] ABSTRACT

The invention discloses 2-oxo- and 2-thioxo-1,3-dithiol compounds of the formula I below which have an advantageous action on plant metabolism. They selectively promote the formation of separation tissue on fruit and leaves and are suitable for facilitating the harvesting of olives and citrus fruit. The compounds have the formula

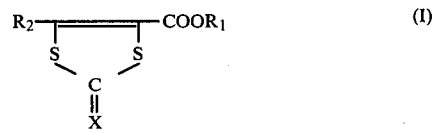

wherein $R_1$ is $C_1$–$C_8$alkyl optionally interrupted by one or more oxygen atoms or substituted by halogen or substituted or unsubstituted phenyl or phenoxy, unsubstituted or halogen-substituted $C_3$–$C_8$alkenyl, $C_3$–$C_8$alkynyl, $C_3$–$C_6$cycloalkyl, or substituted or unsubstituted phenyl, $R_2$ is a hydrogen, methyl, $C_1$–$C_8$alkoxycarbonyl or substituted or unsubstituted phenyl, and X is oxygen or sulfur.

5 Claims, No Drawings

2-OXO- AND 2-THIOXO-1,3-DITHIOL COMPOUNDS AS ACTIVE SUBSTANCES FOR REGULATING PLANT METABOLISM AND THEIR USE

The present invention relates to 2-oxo- and 2-thioxo-dithiol compounds which regulate plant metabolism, processes for their manufacture, compositions which contain them as active ingredients, and a method of regulating plant metabolism, in particular of selectively promoting the formation of separation tissue on fruit and leaves of plants to facilitate harvesting.

The novel 2-oxo-1,3-dithiol and 2-thioxo-1,3-dithiol compounds have the formula

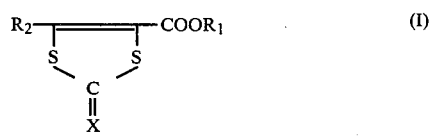

wherein $R_1$ represents $C_1-C_8$ alkyl which can be interrupted by one or more oxygen atoms or substituted by halogen, phenyl or phenoxy, whilst the phenyl nucleus can be substituted by halogen, cyano, nitro, trifluoromethyl, $C_1-C_4$ alkyl, $C_1-C_4$ alkoxy or phenoxy; $C_3-C_8$ alkenyl which is unsubstituted or substituted by halogen; $C_3-C_8$ alkynyl; $C_3-C_6$ cycloalkyl; phenyl which is unsubstituted or substituted by halogen, cyano, nitro, trifluoromethyl, $C_1-C_4$ alkyl, $C_1-C_4$ alkoxy or phenoxy, $C_1-C_4$ alkoxycarbonyl, acetyloxy or dioxy $C_1-C_2$ alkylene; $R_2$ represents hydrogen, methyl, $C_1-C_8$ alkoxycarbonyl, or phenyl which is unsubstituted or substituted by halogen, cyano, nitro, trifluoromethyl, $C_1-C_4$ alkyl, $C_1-C_4$ alkoxy or phenoxy, X represents oxygen or sulfur, with the proviso that, if $R_1$ is methyl, $R_2$ may not be hydrogen or methoxycarbonyl.

Compounds of similar structure are known from the literature, see e.g. J. Org. Chem. 39 2456 (1974), J. Org. Chem. 41 2855 (1976), J. Am. Chem. Soc. 86 5290 (1974) and Ber. 97 1298 (1964). The biological action of these compounds has not yet been described. The 2-oxo-1,3-dithiol and 2-thioxo-1,3-dithiol compounds of the formula I are new and, surprisingly, exert an advantageous action on plant metabolism.

In the compounds of the formula I, alkyl radicals denote branched and straight chain alkyl radicals containing the stated number of carbon atoms, for example methyl, ethyl, n-propyl and isopropyl, n-butyl, sec-butyl, isobutyl and tert-butyl radicals, and also the straight chain and branched pentyl, hexyl, heptyl or octyl radicals. The same applies also to the alkoxy radicals. The alkyl radical $R_1$ can be substituted by halogen or phenyl or interrupted by oxygen atoms. Possible alkenyl or alkynyl radicals $R_1$ are straight chain or branched radicals containing 3 to 8 carbon atoms, preferably the allyl, methyallyl and 2-butenyl radical, as well as the propynyl and butynyl radicals. The phenyl radicals can be unsubstituted or mono- or trisubstituted as defined. Possible cycloalkyl radicals are cyclopropyl, cyclobutyl, cyclopentyl and cyclohexyl.

The 2-oxo-1,3-dithiol and 2-thioxo-1,3-dithiol compounds of the formula I can be obtained in different ways.

Those compounds of the formula I in which $COOR_1$ and $R_2$ represent identical carboxyl esters can be obtained by the method described by L. R. Melby, H. D. Harzter and W. A. Sheppard in J. Org. Chem. 39 2456 (1974) by transesterification, in known manner, of the known 2-thioxo-1,2-dithiol-3,4-dicarboxylate or of its 2-oxo homologue (cf. R. Mayer and B. Gebhardt in Ber. 97 (1964), 1298), with an alcohol of the formula II

wherein $R_2$ is as defined in formula I, or with a reactive derivative (mineral acid ester) thereof.

Asymmetrical compounds of the formula I, i.e. compounds in which $R_2$ is not a carboxyl ester identical with $COOR_1$, can be obtained by reacting a compound of the formula III

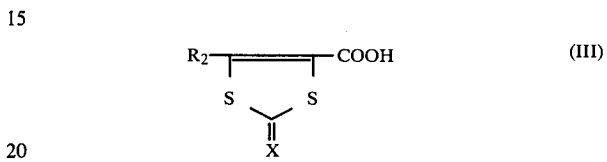

wherein $R_2$ is as defined in formula I, in a manner known per se, with an alcohol of the formula II or with a reactive derivative thereof, or by converting the acid (III) into a reactive derivative (e.g. the acid chloride) and reacting this latter, in a manner known per se, with an alcohol of the formula II.

These transesterification reactions are advantageously carried out under normal pressure and at a temperature between room temperature and the boiling point of the reaction mixture, in an inert solvent or diluent, for example benzene, toluene, ethylene chloride, chloroform or an excess of the alcohol of the formula II. It is also possible to distill off water of condensation from the reaction, e.g. by means of a water separator or, if a mineral acid ester of the alcohol of the formula II has been used, to carry out the reaction to produce the ester in the presence of an acid acceptor.

The compounds of the formula I can furthermore be obtained by reacting a 2-propynylcarboxylate of the formula IV with a dithiocarbonate or trithiocarbonate of the formula V at moderately elevated temperature in accordance with the following reaction scheme:

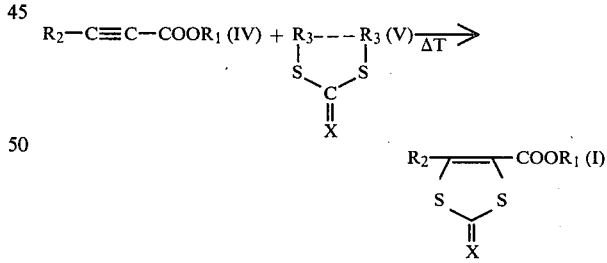

In the above formulae, $R_1$, $R_2$ and X are as defined for formula I and each $R_3$ individually is $C_1-C_4$ alkyl or benzyl, or $R_3—R_3$ as a unit is $C_1-C_4$ alkylene.

The reaction is advantageously carried out in an inert solvent, e.g. toluene or xylene, at moderately elevated temperature between 50° and 150° C. Reference is made in this connection to M. Narita and C. U. Pittmann, Synthesis 1976, 496–514.

Finally, the asymmetrical compound of the formula I, in which $R_2$ does not represent a carboxyl group, can also be obtained by reacting a compound of the formula VI, in accordance with the reaction scheme below, in acid medium to produce a 2-oxo-1,3-dithiol compound, or with sulfur pentoxide to produce a 2-thioxo-1,3-dithiol compound:

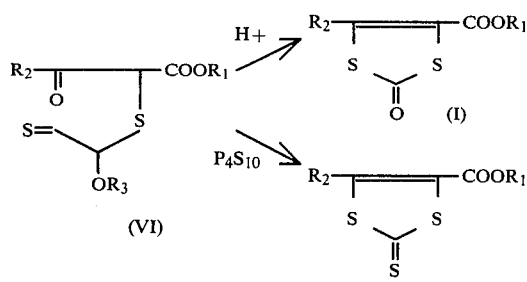

In the above formulae, $R_1$ and $R_2$ are as defined for formula I and $R_3$ is a $C_1$–$C_4$ alkyl or benzyl radical.

These reactions are carried out either in strong aqueous acids (e.g. 80% $H_2SO_4$) or else with phosphorus pentasulfide in decaline, in the temperature range between 30° and 120° C.

2-Oxo-4,5-dicyano-1,3-dithiol and 2-thioxo-4,5-dicyano-1,3-thiol of the formula VIII can be obtained by a method of E. Klingsberg, J. Am. Chem. Soc. 86 5290 (1964), by reacting the sodium salt of dimercaptomaleic acid nitrile of the formula VII with phosgene or thiophosgene:

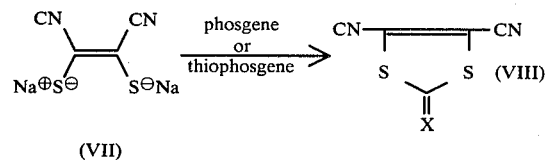

In formula VIII, X represents oxygen or sulfur. This reaction is most desirably carried out in an inert solvent, such as benzene or toluene, at a temperature between 50° and 120° C. These compounds can be converted into compounds of the formula I by saponification of the nitrile groups and subsequent transesterification.

In normal circumstances the compounds of the formula I are usually stable, odourless, crystalline compounds. They are of low toxicity to warm-blooded animals and can be handled without danger. They are most suitable for regulating the metabolism and development of plants. Such action comprises in particular the promotion and facilitation of the abscission of fruit, preferably citrus fruit and olives, which are especially difficult and time-consuming to pick, but also of other fruit which is suitable for mechanical harvesting.

The particular advantage of the compounds of the present invention consists in fact that their use does not result in any phytotoxic side-effects in the fruit, leaves and other parts of the plants. The improvement in the fruit abscission, i.e. the substantial reduction of the plucking force required in manual and mechanical harvesting, entails great advantages in, and also greatly facilitates, the harvesting of large-scale crops, protects fruit-bearing trees and bushes from damage normally caused by tearing off branches and leaves, and is labour-saving.

Various abscission agents and ripening promoters have been proposed, but an account of undesirable side-effects they do not meet the necessary requirements. Thus, for example, "cycloheximide" ($\beta$-[2-(3,5-dimethyl-2-oxocyclohexyl)-2-hydroxyethyl]-glutarimide), despite excellent abscission action on citrus fruit, has the great drawback that it severely damages blossoms and still unripe fruit on the tree, has a pronounced defoliating action, and causes considerable scars on ripe fruit.

$\beta$-Chloroethylphosphoric acid ("ETHREL", "ETPHON") or other alkylene donors have been proposed as ripening promoters and abscission agents, which do not always fulfill the expectations placed in them because of their too pronounced defoliating action.

The active substances of the formula I are not phytotoxic in conventional concentrations employed and have merely low toxicity to warm blooded animals. They do not effect any morphological changes in, or cause damage to, the plants.

To promote the abscission of fruit, especially of olives and citrus fruit, the fruit-bearing trees are treated 3 days to 4 weeks before harvesting with compositions which contain active substances of the formula I.

Experiments have further shown that the compounds of the formula I effect a thinning of blossom and fruit in fruit trees. It is possible to control the time of flowering and the number of blossoms of many ornamental and cultivated plants. This action is particularly important in banana plantations. If all the plants flower simultaneously, then harvesting can take place within a comparatively short space of time. A displacement of the sex differentiation in favour of the female blossoms occurs in cucurbitacaea. Finally, the compound of the present invention stimulate the flow of resin in plants. This is important where resin is industrially utilised, as in collecting latex from rubber trees or obtaining resin from conifers for the production of terpentine oil.

The following Examples describe the manufacture of a number of novel compounds of the formula I. The subsequent table lists further compounds which can be used as active substances. Parts and percentages are by weight.

EXAMPLE 1

Diethyl-2-oxo-1,3-dithiol-4,5-dicarboxylate

A solution of 24 g (0.2 mole) of O,S-ethylene dithiocarbonate (cf. F. N. Jones and U. Andreades, J. Org. Chem., 34, 3001, 1969) and 34 g (0.2 mole) of diethyl aceylenedicarboxylate were refluxed in 100 ml of toluene for 16 hours. After cooling, the solution was concentrated under reduced pressure and the crude product chromatographed on silica gel with ether/hexane (1:3) as eluant, affording the compound of the structure

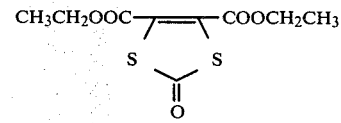

in the form of a yellowish oil with a refractive index of $n_D^{20} = 1.5349$.

EXAMPLE 2

Diethyl-2-thioxo-1,3-dithiol-4,5-dicarboxylae

A solution of 27.2 g (0.2 mole) off ethylene trithiocarbonate and 34 g (0.2 mole) of diethyl acetylenedicarboxylate in 100 ml of toluene was refluxed for 6 hours. After cooling, the solution was concentrated under reduced pressure and the crude product was chromatographed on silica gel with ether/hexane (1:4) as eluant, affording the compound of the structure

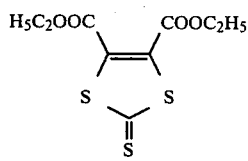

in the form of a yellowish oil with a refractive index of $n_D^{20} = 1.6075$.

The following compounds were obtained in analogous manner:

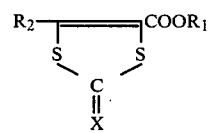

| No. | $R_1$ | $R_2$ | X | Physical constant (°C.) |
|---|---|---|---|---|
| 1 | CH₃ | COOCH₃ | S | m.p 181–3° known |
| 2 | H | COOH | S | m.p 164–6° known |
| 3 | CH₃ | H | S | m.p 106–7° known |
| 4 | H | H | O | m.p 198–9° known |
| 5 | CH₃ | COOCH₃ | O | m.p 64–7° known |
| 6 | C₂H₅ | COOC₂H₅ | O | $n_D^{20} 1.5349$ Example 1 |
| 7 | C₂H₅ | COOC₂H₅ | S | $n_D^{20} 1.6075$ Example 2 |
| 8 | C₃H₇ iso | COOC₃H₇ iso | S | $n_D^{20} 1.5799$ |
| 9 | C₅H₁₁ n | COOC₅H₁₁ n | S | $n_D^{20} 1.5635$ |
| 10 | C₈H₁₇ n | COOC₈H₁₇ n | S | $n_D^{20} 1.5404$ |
| 11 | C₃H₇ iso | H | S | $n_D^{20} 1.6440$ |
| 12 | C₅H₁₁ n | H | S | $n_D^{20} 1.6181$ |
| 13 | C₈H₁₇ n | H | S | $n_D^{20} 1.5839$ |
| 14 | CH₂—C₆H₅ | H | S | m.p 65–6° |
| 15 | C₆H₅ | H | S | m.p 108–9° |
| 16 | CH₂C≡CH | H | S | m.p 65–6° |
| 17 | CH₂CH=CH—CH₃ | H | S | $n_D^{20} 1.6556$ |
| 18 | CH₂—C≡C—CH₃ | H | S | m.p 71–3° |
| 19 | C₃H₆—CH=CH₂ | H | S | $n_D^{20} 1.6343$ |
| 20 | cyclohexyl | H | S | m.p 57–9° |
| 21 | cyclohexyl | H | S | $n_D^{20} 1.6432$ |
| 22 | 4-Cl-C₆H₄ | H | S | m.p 133–5° |
| 23 | 3-Cl-C₆H₄ | H | S | m.p 106–7° |
| 24 | 2-Cl-C₆H₄ | H | S | m.p 132–4° |
| 25 | 3-Br-C₆H₄ | H | S | m.p 112–14° |
| 26 | —C₆H₄—C(CH₃)₂—C₆H₅ | H | S | m.p 101–2° |
| 27 | 3,4-Cl₂-C₆H₃ | H | S | m.p 113–4° |
| 28 | 3,4-methylenedioxy-C₆H₃ (OCH-O) | H | S | m.p 159–60° |
| 29 | 3,4-(CH₃)₂-C₆H₃ | H | S | m.p 96–9° |
| 30 | 4-Br-3,5-(CH₃)₂-C₆H₂ | H | S | m.p 144–5° |
| 31 | 4-C₂H₅-C₆H₄ | H | S | m.p 80–2° |
| 32 | 4-CH₃-C₆H₄ | H | S | m.p 86–8° |
| 33 | 3-OCH₃-C₆H₄ | H | S | m.p 104–5° |
| 34 | 4-NO₂-C₆H₄ | H | S | m.p 148–50° |
| 35 | 4-CN-C₆H₄ | H | S | m.p 160–63° |
| 36 | 4-COOCH₃-C₆H₄ | H | S | m.p 130–2° |
| 37 | 4-OCOCH₃-C₆H₄ | H | S | m.p 120–2° |
| 38 | 4-CF₃-C₆H₄ | H | S | m.p 111–2° |
| 39 | 3,4-Cl₂-C₆H₃ | CH₃ | O | m.p 88–9° |
| 40 | C₂H₅ | CH₃ | S | $n_D^{20} 1.5556$ |
| 41 | CH₂—C≡CH | CH₃ | O | m.p 73–5° |
| 42 | cyclohexyl | CH₃ | O | $n_D^{20} 1.5561$ |
| 43 | CH₂—C₆H₄—Cl (4) | CH₃ | O | m.p 120–1° |
| 44 | CH₂—C₆H₃—Cl₂ (3,4) | CH₃ | O | m.p 106–8° |
| 45 | CH₂—C₆H₄—CH₃ | CH₃ | O | m.p 75–6° |
| 46 | CH₂—C₆H₅ | H | S | m.p 65–7° |

-continued $$R_2-\overset{S}{\underset{\underset{X}{\overset{\|}{C}}}{\diagdown}}\overset{COOR_1}{\underset{S}{\diagup}}$$

| No. | $R_1$ | $R_2$ | X | Physical constant (°C.) |
|---|---|---|---|---|
| 47 | CH$_2$—C$_6$H$_4$—Cl | H | S | m.p 89–90° |
| 48 | CH$_2$—C$_6$H$_4$—CN | H | S | m.p 133–5° |
| 49 | CH$_2$—C$_6$H$_4$—NO$_2$ | H | S | m.p 142–3° |
| 50 | CH$_2$—C$_6$H$_4$—Cl | H | S | m.p 99–100° |
| 51 | CH$_2$—C$_6$H$_3$(Cl)—Cl | H | S | m.p 111–2° |
| 52 | CH$_2$—C$_6$H$_4$—C$_2$H$_5$ | H | S | $n_D^{20}$ 1.6529 |
| 53 | CH$_2$—C$_6$H$_4$—C$_2$H$_5$ | H | S | $n_D^{20}$ 1.6529 |
| 54 | CH$_2$—C$_6$H$_4$—CH$_3$ | H | S | m.p 79–81° |
| 55 | CH$_2$—C$_6$H$_4$—Br | H | S | m.p 116–17° |
| 56 | CH$_2$—C$_6$H$_4$—Cl | H | S | m.p 53–5° |
| 57 | CH$_2$—C$_6$H$_4$—Br | H | S | m.p 78–80° |
| 58 | CH$_2$—C$_6$H$_4$—O—C$_6$H$_5$ | H | S | m.p 76–8° |
| 59 | C$_2$H$_5$ | —C$_6$H$_5$ | O | m.p 84–5° |
| 60 | C$_2$H$_4$OC$_3$H$_7$ iso | H | S | $n_D^{20}$ 1.6101 |
| 61 | CH(CH$_3$)CH$_2$OCH$_3$ | H | S | $n_D^{20}$ 1.6278 |
| 62 | C$_2$H$_5$ | —C$_6$H$_4$—F | O | m.p 95–97° |
| 63 | —C$_6$H$_3$(Cl)—Cl | —C$_6$H$_5$ | O | m.p 154–7° |
| 64 | CH$_3$—C≡CH | CH$_3$ | O | m.p 73–5° |
| 65 | —C$_6$H$_{11}$ | CH$_3$ | O | $n_D^{20}$ 1.5561 |
| 66 | —C$_6$H$_3$(Cl)—Cl | CH | O | m.p 98–9° |
| 67 | C$_4$H$_9$ n | CH$_3$ | O | $n_D^{20}$ 1.5366 |
| 68 | C$_3$H$_7$ iso | CH$_3$ | O | $n_D^{20}$ 1.5372 |
| 69 | —C$_6$H$_3$(NO$_2$)—NO$_2$ | CH$_3$ | O | m.p 143–5° |
| 70 | C$_2$H$_4$OCH$_3$ | CH$_3$ | O | $n_D^{20}$ 1.5481 |
| 71 | C$_2$H$_4$Cl | CH$_3$ | O | $n_D^{20}$ 1.5710 |
| 72 | C$_2$H$_4$Br | CH$_3$ | O | $n_D^{20}$ 1.5919 |
| 73 | C$_3$H$_6$Br | CH$_3$ | O | $n_D^{20}$ 1.5809 |
| 74 | C$_2$H$_4$O—C$_6$H$_4$—Cl | H | S | m.p 139–40° |
| 75 | C$_2$H$_4$O—C$_6$H$_4$—C$_3$H$_7$ iso | H | S | $n_D^{20}$ 1.6108 |
| 76 | C$_2$H$_4$O—C$_6$H$_4$—Cl | H | S | $n_D^{20}$ 1.6676 |
| 77 | (C$_2$H$_4$O)$_2$C$_2$H$_5$ | H | S | $n_D^{20}$ 1.6088 |
| 78 | (C$_2$H$_4$O)$_2$C$_4$H$_9$n | H | S | $n_D^{20}$ 1.5842 |
| 79 | (C$_2$H$_4$O)$_3$CH$_3$ | H | S | $n_D^{20}$ 1.5964 |
| 80 | C$_2$H$_4$—C$_6$H$_4$—OCH$_3$ | H | S | m.p. 73–5° |
| 81 | C$_3$H$_6$—C$_6$H$_4$—CH$_3$ | H | S | m.p 76–8° |
| 82 | C$_3$H$_6$—C$_6$H$_4$—Cl | H | S | m.p 110–2° |
| 83 | C$_4$H$_8$—C$_6$H$_4$—CH$_3$ | H | S | m.p 94–5° |
| 84 | C$_4$H$_8$—C$_6$H$_4$—Cl | H | S | m.p 65–8° |
| 85 | C$_4$H$_8$—C$_6$H$_4$—OCH$_3$ | H | S | m.p 88–90° |
| 86 | (C$_2$H$_4$O)$_3$C$_2$H$_5$ | H | S | $n_D^{20}$ 1.5955 |
| 87 | C$_2$H$_5$ | —C$_6$H$_4$—NO$_2$ | O | m.p 98–9° |
| 88 | CH$_2$—C$_6$H$_3$(Cl)—Cl | —C$_6$H$_5$ | O | m.p 89–90° |

The compounds of the formula I are able to regulate plant metabolism. They promote in particular the ripening of fruit and the formation of separation tissue, especially between fruit and stem. Fruit of all kinds, for example stone fruit (olives) and citrus fruit, such as oranges, lemons, grapefruit etc., can thereby be detached from the stems manually or mechanically without exerting great force. The damage normally caused to the leaves and branches of the plant when the trees and branches are shaken during harvesting and when the fruit is plucked off is to a large extent avoided and the productivity of the trees thus increased.

The extent and nature of the action of the compounds of the formula I depend on the most widely differing factors which vary according to the species of plant, in particular on the concentration, the time of application with regard to the development stage of the plant, and the fruit. Accordingly, for example, plants whose fruit is used or processed are treated directly after flowering or in the corresponding interval of time from harvesting. Application is made preferably in the form of liquid compositions both to the parts of plants above the soil and into and onto the soil. The preferred mode of application is to the parts of plants above the soil, for which purpose solutions or aqueous dispersions are most suitable.

The active substances (compounds) of the formula I are used together with suitable carriers and/or other adjuvants. Suitable carriers and adjuvants can be solid or liquid and correspond to the substances conventionally used in the art of formulation, for example natural or regenerated mineral substances, solvents, dispersants, wetting agents, tackifiers, thickening agents or binders.

The rates of application depend substantially on the end-use application and on the nature of the application (treatment of soil or parts of plant). The conventional rates of application for soil treatment and in areas of arable land are between 0.1 and 10 kg of active substance per hectare of plant crop, preferably between 0.4 and 4 kg of active substance per hectare.

The compositions for promoting abscission and advancing ripening which contain active compounds of the formula I can be formulated as non-aqueous solutions, dispersions, emulsifiable concentrates, wettable powders or as dusts, to which antioxidants, for example hydroquinone, can be added. Such formulations can contain 2 to 95%, preferably 80 to 90%, by weight of active substance, and can be prepared by the techniques conventionally employed in agricultural chemistry. Aqueous preparations having a content of 0.01 to 1% of a non-ionic wetting agent are preferred.

The time of application for the abscission of fruit is shortly before harvesting, i.e. 3 days to 4 weeks before harvesting, and, for the advancement of ripening, shortly before or after the picking of fruit.

The following methods were employed to determine the abscission action on citrus plants:

Parts of branches of orange trees (Navel variety) bearing at least 20 fruit were sprinkled with active substance solutions shortly before harvesting.

Evaluation was made after 7 days, using two different systems:

(a) measurement of the plucking force and its percentage decrease in relation to the untreated control;
(b) the number of fruit that have fallen without shaking expressed in %, compared with untreated control.

While causing no or only slight leaf drop, the tested compounds effected a pronounced formation of separation tissue on the fruit stems, a marked reduction in the plucking force, and many even had good fruit drop values.

| Active substance | Concentration | Reduction of plucking force | fallen oranges |
|---|---|---|---|
| Example 1 | 4000 ppm | 60% | 40 % |
| Example 1 | 2000 ppm | 44% | 33 % |
| Example 1 | 1000 ppm | 19% | 22 % |
| — | Control | 0% (8.9 kg) | 0 % |

Similar experiments were carried out on olive trees. Parts of branches were sprayed with a strongly diluted active substance solution 8 days before the expected time of harvesting, while simultaneously counting the number of olives on the respective part of the branch.

Similarly large parts of branches on the same tree were left untreated as control. After 8 days the branches were uniformly shaken by hand. Whereas 90 to 100% of the olives were shaken down from the treated parts of the branches, 30 to 60% of the fruit remained on the branches of the untreated controls.

The compositions of the present invention are obtained in known manner by intimately mixing and/or grinding active substances of the formula I with suitable carriers, with or without the addition of dispersants or solvents which are inert towards the active substances. The active substances may be processed to the following formulations:

Solid formulations
  dust, tracking powders, granules (coated granules, impregnated granules and homogeneous granules);
  active substance concentrates which are dispersible in water:
  wettable powders, pastes, emulsifiable concentrates.
Liquid formulations:
  solutions.

Solid formulations (dusts, tracking powders, granules) are obtained by mixing the active substances with solid carriers. Suitable carriers are, for example: kaolin, talc, bolus, loess, chalk, limestone, ground limestone, attaclay, dolomite, diatomaceous earth, precipitated silica, alkaline earth silicates, sodium and potassium aluminium silicates (feldspar and mica), calcium and magnesium sulfates, magnesium oxide, ground synthetic materials, fertilisers, for example ammonium sulfate, ammonium phosphate, ammonium nitrate, urea, ground vegetable products, such as corn meal, bark dust, sawdust, nutshell meal, cellulose powder residues of plant extractions, activated charcoal etc. These substances can either be used singly or in admixture with one another.

The granular size of the carriers for dusts is advantageously up to about 0.1 mm, for tracing powders about 0.075 to 0.2 mm, and for granules 0.2 mm or greater.

The concentrations of active substance in the solid formulations are 0.5 to 80%.

To these mixtures can also be added additives which stabilize the active substance and/or nonionics, anionics and cationics, which, for example, improve the adhesion of the active ingredients on plants or parts of plants (tackifiers and agglutinants) and/or ensure a better wettability (wetting agents) and dispersibility (dispersing agents).

Examples of suitable agglutinants are: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl moiety, ligninsulfonic acids, the alkali metal and alkaline earth metal salts thereof, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

Water-dispersible concentrates, i.e. wettable powders, pastes and emulsifiable concentrates, are compositions which can be diluted with water to the desired concentration. They consist of active substance, carrier, optionally additives which stabilize the active substance, surface-active substances and antifoams and, if appropriate, solvents. The concentrations of active substance in these compositions is 5 to 80%.

Wettable powders and pastes are obtained by mixing and grinding the active substances with dispersing agents and powdery carriers in suitable devices until homogeneity is attained. Suitable carriers are, for example, those already mentioned for the solid formulations.

It is often advantageous to use mixtures of different carriers. As dispersing agents there can be used, for example, condensation products of sulfonated naphthalene and sulfonated naphthalene derivatives with formaldehyde, condensation products of naphthalene or naphthalenesulfonic acids with phenyl and formaldehyde, as well as alkali metal, ammonium and alkaline earth metal salts of ligninsulfonic acid, in addition, alkylarylsulfonates, alkali metal and alkaline earth metal salts of dibutylnaphthalenesulfonic acid, fatty alcohol sulfates, such as salts of sulfated hexadecanols, heptadecanols, octadecanols, and salts of sulfated fatty alcohol glycol ethers, the sodium salt of oleylmethyltauride, ditertiary acetylene glycols, dialkyldilaurylammonium chloride and fatty acid alkali metal and alkaline earth metal salts.

Suitable antifoams are, for example, silicones.

The active substances are mixed, ground sieved and strained with the above additives such that, in wettable powders, the solid particle size of 0.02 to 0.04 mm and in pastes, of 0.03 mm, is not exceeded. Emulsifiable concentrates and pastes are formulated by using dispersing agents, such as those cited previously above, organic solvents, and water. Examples of suitable solvents are: alcohols, benzene, xylenes, toluene, dimethyl sulfoxide, and mineral oil fractions which boil between 120° and 350° C. The solvents must be practically odourless, not phytotoxic, inert to the active substances and may not be readily inflammable.

Furthermore, the compositions of the invention can be applied in the form of solutions. For this purpose the active substances or several active substances of the general formula I are dissolved in suitable organic solvents, mixtures of solvents, or in water. Aliphatic and aromatic hydrocarbons, chlorinated derivatives thereof, alkylnaphthalenes and mineral oils, by themselves or in admixture, can be used as organic solvents. The solutions will contain the active substances in a concentration from 1 to 20%.

The compositions of this invention can be mixed with other biocidally active substances or agents. Thus in order to broaden the activity spectrum, the compositions may contain, for example, insecticides, fungicides, bactericides, fungistats, bacteriostats or nematocides, in addition to the compounds of the general formula I. The compositions of the invention may additionally contain plant fertilisers, trace elements and the like.

Formulations of the novel active compounds of the formula I are described hereinafter. The parts denote parts by weight.

The active substance is mixed with epichlorohydrin and the mixture is dissolved in 6 parts of acetone; the polyethylene glycol and cetylpolyethylene glycol ether are then added. The resulting solution is sprayed on kaolin, and the acetone is subsequently evaporated in vacuo.

Wettable powders

The following constituents are used to formulate (a) a 50%, (b) a 25% and (c) a 10% wettable powder:

(a) 50 parts of diethyl-2-thioxo-1,3-dithiol-4,5-dicarboxylate
  5 parts of sodium dibutylnaphthylsulfonate,
  3 parts of naphthalenesulfonic acid/phenolsulfonic acid/formaldehyde concentrate (3:2:1),
  20 parts of kaolin,
  22 parts of Champagne chalk;
(b) 25 parts of the above active substance,
  5 parts of sodium oleylmethyltauride,
  2.5 parts of naphthalenesulfonic acid/formaldehyde condensate
  0.5 parts of carboxymethyl cellulose,
  5 parts of neutral potasium aluminium silicate,
  62 parts of kaolin;
(c) 10 parts of the above active substance,
  3 parts of a mixture of the sodium salts of saturated alcohol sulfates,
  5 parts of naphthalenesulfonic acid/formaldehyde condensate,
  82 parts of kaolin.

The indicated active substance is applied to the corresponding carriers (kaolin and chalk) and then these are mixed and ground, affording wettable powders of excellent wettability and suspension power. By diluting these wettable powders with water it is possible to obtain suspensions of the desired concentration of active substance.

Granules

The following substances are used to formulate 5% granules:

5 parts of dimethyl-2-thioxo-1,3-dithiol-4,5-dicarboxylate
  0.25 parts of epichlorohydrin,
  0.25 parts of cetylpolyethylene glycol ether with 8 moles of ethylene oxide,
  3.50 parts of polyethylene glycol,
  91 parts of kaolin (particle size 0.3–0.8 mm).

The active substance is mixed with epichlorohydrin and the mixture is dissolved in 6 parts of acetone; the polyethylene glycol and cetylpolyethylene glycol ether are then added. The resulting solution is sprayed on kaolin, and the acetone is subsequently evaporated in vacuo.

Paste

The following substances are used to formulate a 45% paste:

45 parts of diisopropyl-2-oxo-1,3-dithiol-4,5-dicarboxylate
  5 parts of sodium aluminium silicate,
  14 parts of cetylpolyethylene glycol ether with 8 moles of ethylene oxide,
  1 part of oleylpolyethylene glycol ether with 5 moles of ethylene oxide,
  2 parts of spindle oil,
  10 parts of polyethylene glycol,
  23 parts of water.

The active substance is homogeneously mixed with the adjuvants in appropriate devices and ground, yielding a paste from which, by dilution with water, it is possible to obtain suspension of the desired concentration of active substance.

Emulsifiable Concentrate

The following ingredients are mixed to formulate a 25% emulsifiable concentrate:

25 parts of dibenzyl-2-thioxo-1,3-dithiol-4,5-dicarboxylate 5 parts of a mixture of nonylphenolpolyoxyethylene and calcium dodecylbenzenesulfonate, 3 parts of 3,5,5-trimethyl-2-cyclohexen-1-one, 35 parts of dimethyl formamide.

This concentrate can be diluted with water to produce emulsions of suitable concentrations.

What is claimed is:

1. A method of regulating plant metabolism which comprises applying to said plant an effective amount of a compound of the formula

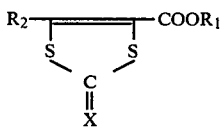

wherein $R_1$ represents $C_1$–$C_8$alkyl which can be interrupted by one or more oxygen atoms or substituted by halogen, phenyl or phenoxy, whilst the phenyl nucleus can be substituted by halogen, cyano, nitro, trifluoromethyl, $C_1$–$C_4$alkyl, or phenoxy; $C_3$–$C_8$alkenyl which is unsubstituted or substituted by halogen; $C_3$–$C_8$alkynyl; $C_3$–$C_6$cycloalkyl; phenyl which is unsubstituted or substituted by halogen, cyano, nitro, trifluoromethyl, $C_1$–$C_4$alkyl, $C_1$–$C_4$alkoxy or phenoxy, $C_1$–$C_4$alkoxycarbonyl, acetyloxy or dioxy-$C_1$–$C_2$alkylene; $R_2$ represents hydrogen, methyl, $C_1$–$C_8$alkoxycarbonyl, or phenyl which is unsubstituted or substituted by halogen, cyano, nitro, trifluoromethyl, $C_1$–$C_4$alkyl, $C_1$–$C_4$alkoxy or phenoxy, X represents oxygen or sulfur.

2. A method of promoting the abscission of fruit which is ripe for harvesting which comprises applying to said fruit an effective amount of a compound of the formula

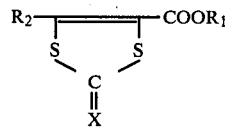

wherein $R_1$ represents $C_1$–$C_8$alkyl which can be interrupted by one or more oxygen atoms or substituted by halogen, phenyl or phenoxy, whilst the phenyl nucleus can be substituted by halogen, cyano, nitro, trifluoromethyl, $C_1$–$C_4$alkyl, or phenoxy; $C_3$–$C_8$alkenyl which is unsubstituted or substituted by halogen; $C_3$–$C_8$alkynyl; $C_3$–$C_6$cycloalkyl; phenyl which is unsubstituted or substituted by halogen, cyano, nitro, trifluoromethyl, $C_1$–$C_4$alkyl, $C_1$–$C_4$alkoxy or phenoxy, $C_1$–$C_4$alkoxycarbonyl, acetyloxy or dioxy-$C_1$–$C_2$alkylene; $R_2$ represents hydrogen, methyl, $C_1$–$C_8$ alkoxycarbonyl, or phenyl which is unsubstituted or substituted by halogen, cyano, nitro, trifluoromethyl, $C_1$–$C_4$alkyl, $C_1$–$C_4$alkoxy or phenoxy, X represents oxygen or sulfur.

3. A method according to claim 2 in which the fruit is citrus fruit or olives.

4. A method according to claim 3 in which the fruit is oranges and the compound applied is diethyl-2-oxo-1,3-dithiol-4,5-dicarboxylate.

5. A method according to claim 3 in which the fruit is oranges and the compound applied is methyl-2-oxo-1,3-dithiol-4-methyl-5-carboxylate.

* * * * *